United States Patent
Beale

(10) Patent No.: US 9,687,488 B2
(45) Date of Patent: Jun. 27, 2017

(54) COMPOSITIONS AND METHODS FOR INCREASING NEUROTROPHIC PEPTIDES

(71) Applicant: Saint Louis College of Pharmacy, St. Louis, MO (US)

(72) Inventor: John M. Beale, Manchester, MO (US)

(73) Assignee: ST. LOUIS COLLEGE OF PHARMACY, St. Louis, MO (US)

(*) Notice: Subject to any disclaimer, the term of this patent is extended or adjusted under 35 U.S.C. 154(b) by 0 days.

(21) Appl. No.: 14/398,704

(22) PCT Filed: May 3, 2013

(86) PCT No.: PCT/US2013/039508
§ 371 (c)(1),
(2) Date: Nov. 3, 2014

(87) PCT Pub. No.: WO2013/166413
PCT Pub. Date: Nov. 7, 2013

(65) Prior Publication Data
US 2015/0126531 A1    May 7, 2015

Related U.S. Application Data

(60) Provisional application No. 61/642,086, filed on May 3, 2012.

(51) Int. Cl.
*A61K 31/519* (2006.01)
*A61K 31/095* (2006.01)
(Continued)

(52) U.S. Cl.
CPC .......... *A61K 31/519* (2013.01); *A61K 31/095* (2013.01); *A61K 31/167* (2013.01); *A61K 31/18* (2013.01); *A61K 31/381* (2013.01)

(58) Field of Classification Search
CPC .................................................. A61K 31/519
(Continued)

(56) References Cited

U.S. PATENT DOCUMENTS

| 8,129,394 B2 | 3/2012 | Hunag et al. |
| 8,168,654 B2 | 5/2012 | Collingwood et al. |

(Continued)

FOREIGN PATENT DOCUMENTS

| CN | 101906105 | 8/2010 |
| CN | 104470515 B | 12/2016 |

(Continued)

OTHER PUBLICATIONS

CN Search Report of corresponding application CN Publication No. 201380023195.5 mailed Jan. 6, 2016.
(Continued)

*Primary Examiner* — Shengjun Wang
(74) *Attorney, Agent, or Firm* — Polster Lieder Woodruff & Lucchesi L.C.

(57) ABSTRACT

A pharmaceutical composition is provided which includes a pharmaceutically acceptable excipient and a pharmaceutically and physically acceptable amount of a compound selected from the group consisting of Chemical Formulas I-IV as described herein, or a pharmaceutically acceptable salt thereof. Also provided are methods of increasing a level of a defined neurotrophic peptide in an organism or tissue comprising the administration of a pharmaceutically and physically acceptable amount of one or more of the compositions described above, and a method for treating a neurodegenerative disease in a subject in need thereof, the method comprising administering a therapeutically effective amount of the pharmaceutical composition of claim 1.

15 Claims, 6 Drawing Sheets

Sortilin.

(51) Int. Cl.
*A61K 31/18*      (2006.01)
*A61K 31/381*     (2006.01)
*A61K 31/167*     (2006.01)

(58) Field of Classification Search
USPC .................................................. 514/259.31
See application file for complete search history.

(56) References Cited

U.S. PATENT DOCUMENTS

2009/0171086 A1   7/2009  Singh et al.
2011/0136880 A1   6/2011  El Sayed et al.
2012/0088775 A1   4/2012  Zhang et al.

FOREIGN PATENT DOCUMENTS

EP     0970084 B1     6/2003
EP     2415765 A1     2/2012
WO     2008076262 A2  6/2008
WO     2010022175 A1  2/2010
WO     2010141074 A2  12/2010

OTHER PUBLICATIONS

International Search Report of corresponding application PCT/US2013/039508 mailed Oct. 29, 2013.
Supplementary Partial EPO Search Report of corresponding application EPO Application No. 13784625.9 mailed Nov. 10, 2015.
Database Registry (online) Chemical Abstracts Service, Columbus, Ohio, US, Feb. 28, 2005.

FIGURE 1: Sortilin.
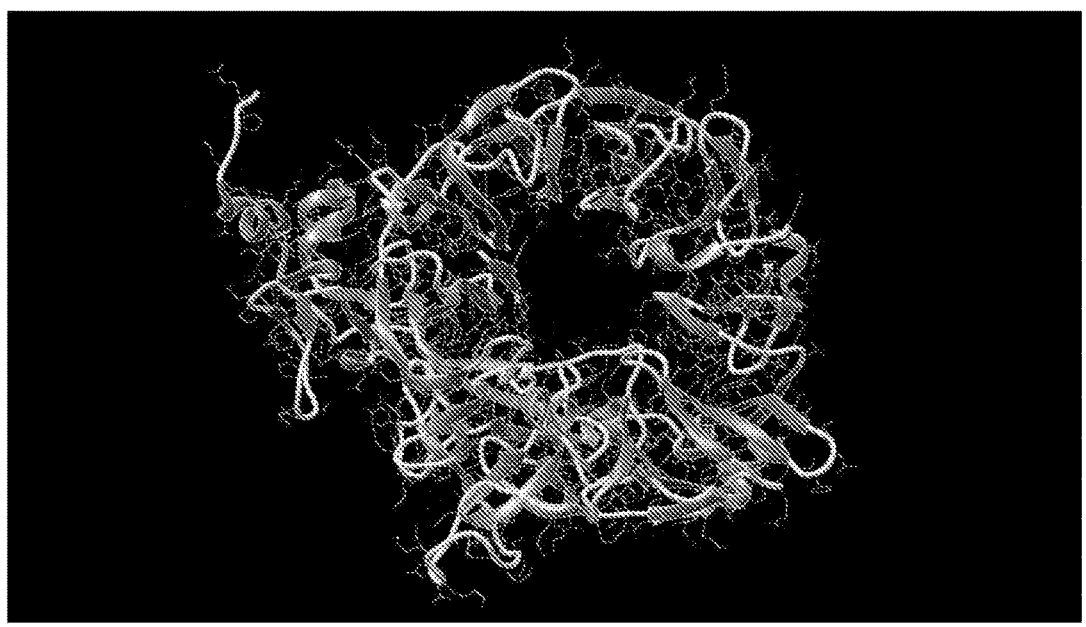

Figure 2; Terminal residues of neurotensin bound to sortilin
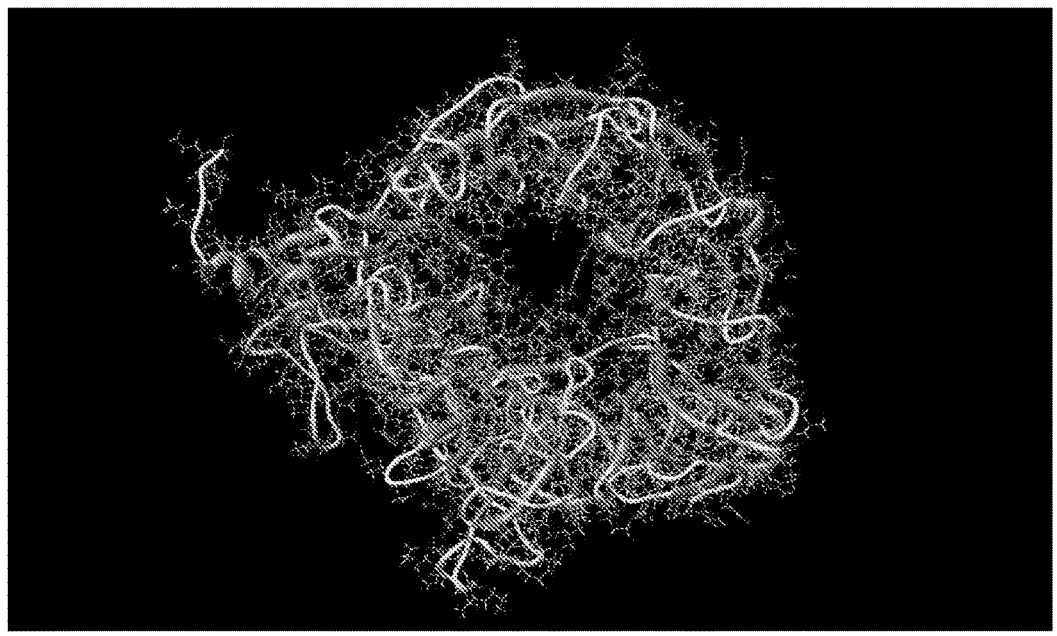

Figure 3; Terminal 10 residues of progranulin bound to sortilin

Figure 4; The SMN protein
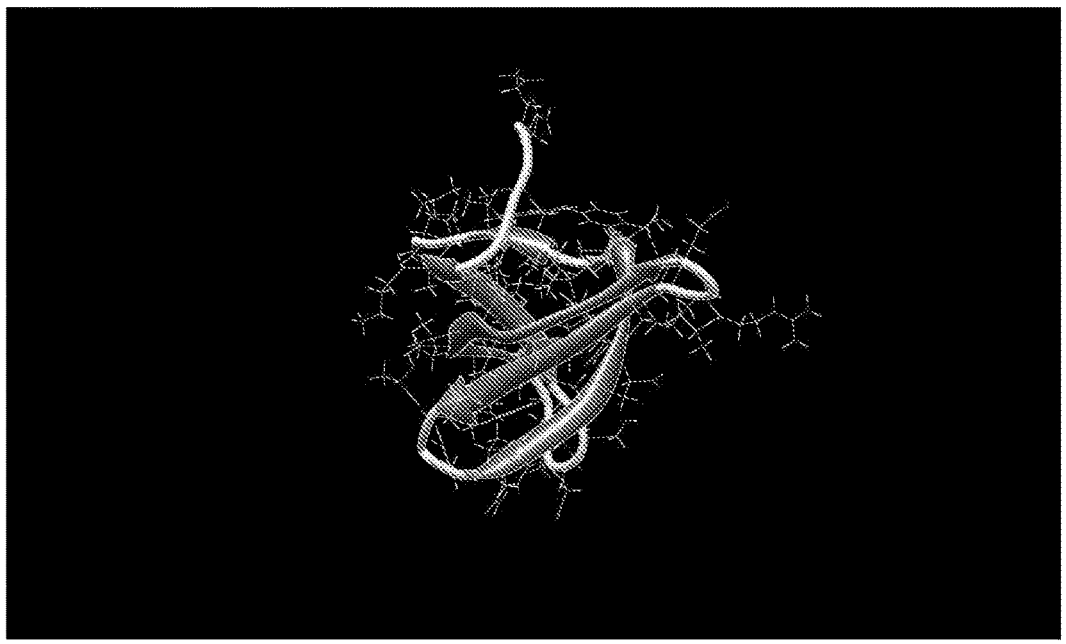

Figure 5; Dot blot experiments
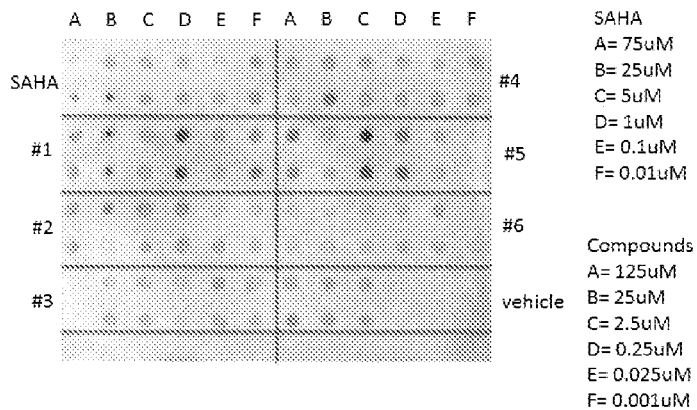
Compound #1 at 250nM (~3 fold increase) and #5 at 2.5uM (~4 fold increase)

Figure 6; SMN Immunoblotting Experiments
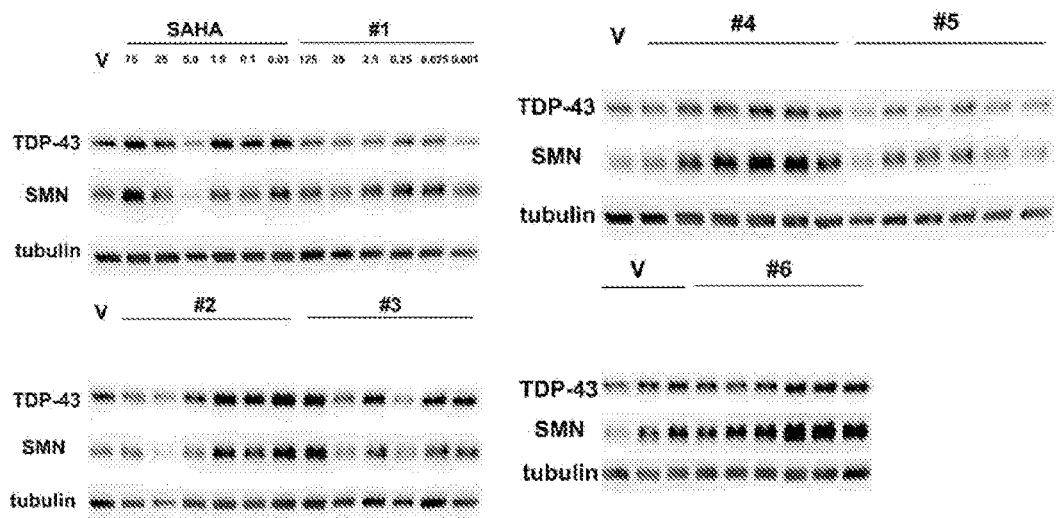

COMPOSITIONS AND METHODS FOR INCREASING NEUROTROPHIC PEPTIDES

CROSS-REFERENCE TO RELATED APPLICATIONS

This application is the United States National Stage under 35 U.S.C. § 371 of International Application Serial No. PCT/US2013/039508, filed on May 3, 2013 which claims priority to U.S. Provisional Application Ser. No. 61/642,086 filed May 3, 2012,which are incorporated by reference in their entirety.

STATEMENT REGARDING FEDERALLY SPONSORED RESEARCH OR DEVELOPMENT

This invention was made with government support under Beale FRIF 20-141-9770-6660. The government has certain rights to rights in the invention.

INCORPORATION-BY-REFERENCE OF MATERIAL SUBMITTED ON A COMPACT DISC

Not applicable.

BACKGROUND OF THE INVENTION

1. Field of the Invention

The present invention relates to pharmaceutical compositions and methods for increasing neurotrophic peptides related to the antagonism of sortilin.

2. Description of Related Art

Sortilin (see FIG. 1) is a toroid protein that is involved in the trafficking of other proteins, notably neurotensin, amyloid-beta precursor protein, and progranulin (PRGN). In the case of progranulin, sortilin is one of the primary receptors, the other being tumor necrosis factor receptor (TNFR). In the neurons, PRGN is removed by sortilin-mediated endocytosis. Brain PRGN is known to be haploinsufficient (about 50% of normal) in patients with frontotemporal dementia (FTD). This condition causes degeneration of the frontal lobe of the brain, and is progressive with age. FTD is associated with behavioral changes, speech and language problems, and in rarer cases motor disorders that resemble Parkinsonism. Without being bound to a particular theory, it is believed that FTD is due primarily to deletions or mutations in the PRGN gene. Mutations in the PRGN gene, e.g., have been identified as a major cause of frontotemporal lobar disease, with ubiquitin-positive inclusions (FTLD-U). There is currently no effective pharmacological treatment for FTD.

Another protein, the survival motor neuron (SMN) protein that is found in cortical neurons, is known to be present at levels far below normal in patients with spinal muscular atrophy (SMA). This disorder, in which neural support of muscle integrity is lacking, is fairly common and is fatal in infants. SMA also occurs in older patients. It is a neuromuscular disease characterized by the specific degeneration of SMN protein. Without being bound to a particular theory, it is believed that this is due primarily to deletions or mutations in the SMN1 gene. Currently there is no effective treatment for this disorder. Other diseases and disorders characterized by loss or reduction of SMN protein include motor neuron diseases such as amyotrophic lateral sclerosis (ALS), also called Lou Gehrig's disease.

Thus, the need exists for effective pharmacological and pharmaceutical compositions and methods for increasing the level of defined neurotrophic proteins in humans, and for treating, preventing, inhibiting, or reversing neurodegenerative diseases or conditions in a subject in need thereof wherein the disease or condition is mediated at least in part by the level of said defined neural proteins.

BRIEF SUMMARY OF THE INVENTION

Accordingly, pharmaceutical compositions and methods are provided which address the needs outlined herein. By inhibition of sortilin with small, druglike molecules, the ablation of neurotrophins such as progranulin (PRGN) and survivor motor neuron (SMN) protein, respectively, are reduced or prevented. Thus, levels of defined neurotrophic peptides such as PRGN and SMN in an organism or tissue may be increased or enhanced by the administration of one or more of the compositions described herein. In one embodiment, the invention further provides for the use of one or more compounds of the invention in the manufacture of a medicament for halting or decreasing neurodegenerative diseases, including FTD and SMA. The invention further relates to a method of treating neurodegenerative diseases, including FTD and SMA, in a subject in need of treatment, comprising administering to said subject a therapeutically effective amount of a pharmaceutical composition of the invention. In various embodiments the pharmaceutical composition of the invention may include as an active ingredient a compound represented by the following general formulas and exemplary embodiments:

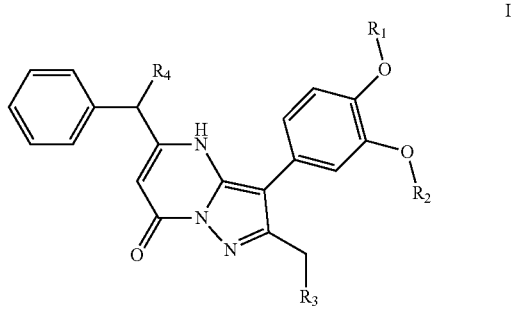

I

Compound 1 $R_1$=$CH_3$, $R_2$=$CH_3$, $R_3$=H, $R_4$=H
Compound 5 $R_1$=$CH_3$, $R_2$=H, $R_3$=H, $R_4$=H
Compound 6 $R_1$=$CH_3$, $R_2$=$CH_3$, $R_3$=OH, $R_4$=H
Compound 7 $R_1$=$CH_3$, $R_2$=$CH_3$, $R_3$=H, $R_4$=OH
Wherein $R_1$=H or $CH_3$, $R_2$=H or $CH_3$, $R_3$=H or OH, and $R_4$=H or OH;

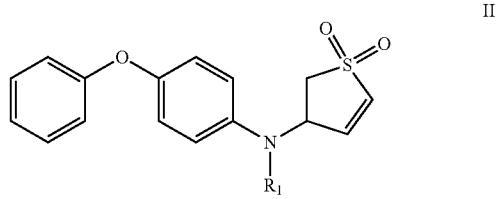

II

Compound 2 $R_1$=$COCH_3$
Compound 8 $R_1$=H
Wherein $R_1$=H or $COCH_3$;

III

Compound 3 R$_1$=CH$_3$ R$_2$=H
Compound 9 R$_1$=H R$_2$=H
Compound 10 R$_1$=CH$_3$ R$_2$=OH
Compound 11 R$_1$=H R$_2$=OH
Wherein R$_1$=H or CH$_3$ and R$_2$=H or OH; and

IV

Compound 4 R$_1$=CH$_3$, R$_2$=H
Compound 12 R$_1$=H, R$_2$=H
Compound 13 R$_1$=CH$_3$, R$_2$=OH
Compound 14 R$_1$=H, R$_2$=OH
Wherein R$_1$=H or CH$_3$ and R$_2$=H or OH.

These and other features, aspects and advantages of the present invention will become better understood with reference to the following description, examples and appended claims.

BRIEF DESCRIPTION OF THE SEVERAL VIEWS OF THE DRAWINGS

The presently disclosed subject matter will be better understood from reading the following description of non-limiting embodiments, with reference to the attached figures, wherein below:

FIG. 1 is a representation of the structure of the protein sortilin, showing the toroid presentation and the secondary structure (depicted in color versions of FIG. 1 as purple ribbons for beta sheets and red ribbons for alpha helices). Sortilin is the receptor site for progranulin as well as for compounds of the invention, as described in the examples for compounds 1-4. The binding site for progranulin, neurotensin, and compounds of the invention is located at approximately 10 o'clock in the figure. Experimental results show that compounds 1-4 possess high affinities (K$_i$ in the micromolar to nanomolar range) for the binding site and in the models prevent the binding of progranulin to sortilin FIG. 2 is a molecular representation of the structure of sortilin with the terminal ten residues of the protein neurotensin bound to the receptor site. This structure was developed through computational molecular docking of the neurotensin surrogate to sortilin.

FIG. 3 is a molecular representation of the structure of the protein sortilin with the terminal ten residues of progranulin bound to the receptor site. This structure was developed through computational molecular docking of the progranulin residues to sortilin.

FIG. 4 is a molecular representation of the structure of the survival motor neuron protein as derived from the RCSB Protein Databank. The secondary structure (beta sheets) is indicated by ribbons.

FIG. 5 shows the dot blot information that indicates the enhancement of progranulin levels in cortical neuron cultures.

FIG. 6 is a picture of the immunoblotting experiments that reveal the enhancement of the SMN protein in cortical neuron cultures. The tubulin line is a housekeeping protein that the concentrations of SMN are determined against. TDP-43 is an unrelated protein.

DETAILED DESCRIPTION

Abbreviations and Definitions

The foregoing summary, as well as the following detailed description of certain embodiments will be better understood when read in conjunction with the appended figures. As used herein, an element or step recited in the singular and proceeded with the word "a" or "an" should be understood as not excluding plural of said elements or steps, unless such exclusion is explicitly stated. Furthermore, references to "one embodiment" or "an embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

As used herein, the term "therapeutically effective amounts" means those amounts that, when administered to a particular subject in view of the nature and severity of that subject's disease or condition, will have the desired therapeutic effect, e.g., an amount which will cure, prevent or at least partially arrest or inhibit the disease or condition.

The term "treating" or "treatment" means any treatment of a disease, including preventing, i.e., causing the clinical symptoms of the disease not to develop; inhibiting, i.e., arresting or counteracting the development of clinical symptoms, as well as relieving, i.e., causing the regression and/or amelioration of clinical symptoms.

The term "excipient" is meant to include any carrier, vehicle, solvent or any more or less inert substance (in terms of the treated disease) added to a pharmaceutical to adjust the composition of the dosage form to the appropriate route of administration.

By "pharmaceutically acceptable salts" is meant those salts that are safe for topical or systemic administration. These salts include the sodium, potassium, calcium, magnesium, and ammonium salts.

Active Compounds

In various embodiments, the present invention includes the use of one or more compounds of the invention in the manufacture of a medicament, or pharmaceutical composition, that treats, inhibits or prevents neurodegenerative diseases. There are a number of disorders that have been implicated by or believed to be mediated at least in part by sortilin activity, where sortilin activity is believed to play a role in triggering disease onset. Disorders of this type that may be amenable to treatment with the compounds of the invention include the following but not limited to: FTD, FTLD-U, SMA, amyotrophic lateral sclerosis (ALS), and Alzheimer's disease.

In various embodiments the pharmaceutical composition of the invention may include as an active ingredient a compound represented by the following general formulas and exemplary embodiments:

I

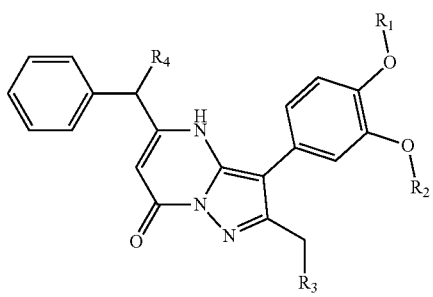

Compound 1 $R_1$=CH$_3$, $R_2$=CH$_3$, $R_3$=H, $R_4$=H
Compound 5 $R_1$=CH$_3$, $R_2$=H, $R_3$=H, $R_4$=H
Compound 6 $R_1$=CH$_3$, $R_2$=CH$_3$, $R_3$=OH, $R_4$=H
Compound 7 $R_1$=CH$_3$, $R_2$=CH$_3$, $R_3$=H, $R_4$=OH
Wherein $R_1$=H or CH$_3$, $R_2$=H or CH$_3$, $R_3$=H or OH, and $R_4$=H or OH;

II

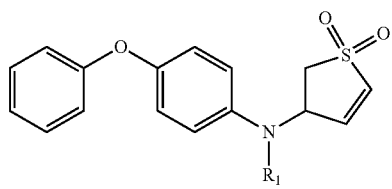

Compound 2 $R_1$=COCH$_3$
Compound 8 $R_1$=H
Wherein $R_1$=H or COCH$_3$;

III

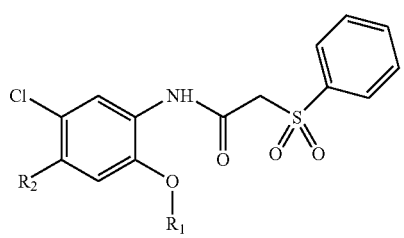

Compound 3 $R_1$=CH$_3$ $R_2$=H
Compound 9 $R_1$=H $R_2$=H
Compound 10 $R_1$=CH$_3$ $R_2$=OH
Compound 11 $R_1$=H $R_2$=OH
Wherein $R_1$=H or CH$_3$ and $R_2$=H or OH; and

IV

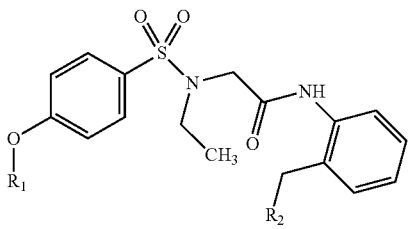

Compound 4 $R_1$=CH$_3$, $R_2$=H
Compound 12 $R_1$=H, $R_2$=H
Compound 13 $R_1$=CH$_3$, $R_2$=OH
Compound 14 $R_1$=H, $R_2$=OH
Wherein $R_1$=H or CH$_3$ and $R_2$=H or OH.

Specific preferred embodiments, Compounds 1-4, of compounds within the scope of general formulas I-IV, respectively, are disclosed as follows:

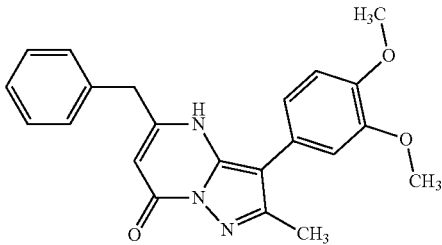

Compound 1: 5-benzyl-3-(3,4-dimethoxyphenyl)-2-methyl-4H,7H-pyrazolo[1,5,a]pyrimidin-7-one; $C_{22}H_{21}N_3O_3$

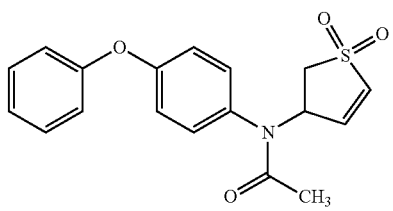 [SMILES: CC(=O)N(c1ccc(Oc2ccccc2)cc1)C1C=CS(=O)(=O)C1]

Compound 2: N-(1,1-dioxo-2,3-dihydro-1-$\square^6$-thio-phene-3-yl)-N-(4-phenoxyphenyl)acetamide; $C_{18}H_{17}NO_4S$

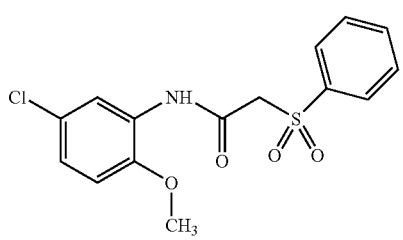 [SMILES: COc1ccc(Cl)cc1NC(=O)CS(=O)(=O)c1ccccc1]

Compound 3: 2-(benzenesulfonyl)-N-(5-chloro-2-methoxyphenyl)acetamide; $C_{15}H_{14}ClNO_4S$

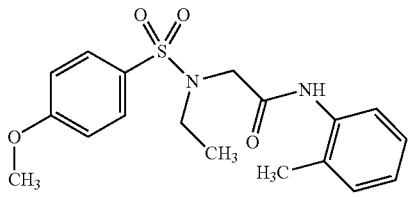 [SMILES: CCN(CC(=O)Nc1ccccc1C)S(=O)(=O)c1ccc(OC)cc1]

Compound 4: 2-(N-ethyl-4-methoxybenzenesulfonamido)-N-(2-methylphenyl) acetamide; $C_{18}H_{22}N_2O_4S$

| CPD | FW | Formula | RB | clogP | $H_{acc}$ | $H_{don}$ | log Sw |
|---|---|---|---|---|---|---|---|
| 1 | 375.4204 | $C_{22}H_{21}N_3O_3$ | 3 | 2.7 | 4 | 1 | −4.243 |
| 2 | 343.3969 | $C_{18}H_{17}NO_4S$ | 4 | 2.17 | 4 | 0 | −3.557 |
| 3 | 339.794 | $C_{15}H_{14}ClNO_4S$ | 4 | 2.01 | 4 | 1 | −3.39 |
| 4 | 362.4433 | $C_{18}H_{22}N_2O_4S$ | 4 | 2.97 | 5 | 1 | −4.37 |

"RB" is the number of rotatable bonds in the respective compounds, "clogP" is the octanol:water partition coefficient (a measure of hydrophilicity and lipophilicity), "$H_{acc}$" is the number of hydrogen bond acceptors, "$H_{don}$" is the number of hydrogen bond donors, and "log Sw" is the water solubility coefficient. $10^{log\ Sw}$=the water solubility of the compound in mol/liter.

Activity of the compounds of the present invention for increasing PRGN and SMN levels in brain neurons can be demonstrated using the procedures outlined in the examples below.

The present invention is also directed to methods and compositions for the prevention and treatment of neurodegenerative diseases, including but not limited to FTD and SMA, comprising administering preferred compositions containing active compounds of the types described herein. The compositions of this invention may be administered to the subject subcutaneously, intravenously/or intramuscularly. In a preferred embodiment, the compositions of this invention are administered to a subject subcutaneously or intramuscularly.

For use in treatment or prophylaxis of subjects, the compounds of the invention can be formulated as pharmaceutical or veterinary compositions. Depending on the subject to be treated, the mode of administration, and the type of treatment desired (e.g., inhibition, prevention, prophylaxis, therapy), the compounds are formulated in ways consonant with these parameters. The compositions of the present invention comprise a therapeutically or prophylactically effective dosage of an active compound. The composition is a sortilin inhibitor as described in more detail above. The active compounds of this invention are used in combination with a pharmaceutically acceptable carrier or excipient.

The compositions of the present invention may be incorporated in conventional pharmaceutical formulations (e.g. injectable solutions) for use in treating humans or animals in need thereof. Pharmaceutical compositions can be administered by subcutaneous, intravenous, or intramuscular injection, or as large volume parenteral solutions and the like.

The term parenteral as used herein includes subcutaneous injections, intravenous, intramuscular, intrasternal injection, or infusion techniques.

For example, a parenteral therapeutic composition may comprise a sterile isotonic saline solution containing between 0.1 percent and 90 percent weight to volume of the active compounds of the invention. A preferred solution contains from about 5 percent to about 25 weight percent active compounds in solution (% weight per volume).

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides.

Total daily dose administered to a subject in single or divided doses may be in amounts, for example, from about 0.00025 to about 20 mg/kg body weight daily, more preferably from about 0.001 to about 10 mg/kg body weight daily, and more usually about 0.01 to about 3 mg/kg body weight daily, when given as a parenteral injection or continuous infusion.

Dosage unit compositions may contain such amounts of sub-multiples thereof to make up the daily dose. The amount of active ingredient that may be combined with the carrier materials to produce a single dosage form will vary depending upon the subject treated and the particular mode of administration. For instance, systems such as transdermal administration or oral administration, which are substantially less efficient delivery systems, may require dosages at least an order of magnitude above those required for parenteral administration. The amount of active ingredient that may be combined with the carrier materials to produce a single dosage form will vary depending upon the host treated and the particular mode of administration. It will be appreciated that the unit content of active ingredients contained in an individual dose of each dosage form need not in itself constitute an effective amount, as the necessary effective amount could be reached by administration of a number of individual doses. The selection of dosage depends upon the dosage form utilized, the condition being treated, and the particular purpose to be achieved according to the determination of those skilled in the art.

The dosage regimen for treating a disease condition with the compounds and/or compositions of this invention is selected in accordance with a variety of factors, including the type, age, weight, sex, diet and medical condition of the patient, the route of administration, pharmacological considerations such as the activity, efficacy, pharmacokinetic and toxicology profiles of the particular compound employed, whether a drug delivery system is utilized and whether the compound is administered as part of a drug combination. Thus, the dosage regimen actually employed may vary widely and therefore may deviate from the preferred dosage regimen set forth above.

The pharmaceutical compositions of the present invention are preferably administered to a human. However, besides being useful for human treatment, these extracts are also useful for veterinary treatment of companion animals, exotic animals and farm animals, including mammals, rodents, avians, and the like. More preferred animals include horses, dogs, cats, sheep, and pigs.

The detailed description set forth above is provided to aid those skilled in the art in practicing the present invention. Even so, this detailed description should not be construed to unduly limit the present invention as modifications and variation in the embodiments discussed herein can be made by those of ordinary skill in the art without departing from the spirit or scope of the present inventive discovery.

Depending upon the particular route of administration, and compatibility with the active compound chosen, a variety of pharmaceutically-acceptable carriers, well-known in the art, may be used. These include solid or liquid filler, diluents, hydrotropes, excipients, surface-active agents, and encapsulating substances. The amount of the carrier employed in conjunction with the catalyst is sufficient to provide a practical quantity of material per unit dose.

Pharmaceutically-acceptable carriers for systemic administration that may be incorporated into the compositions of this invention, include sugars, starches, cellulose and its derivatives, malt, gelatin, talc, calcium sulfate, vegetable oil, synthetic oils, polyols, alginic acid, phosphate buffer solutions, emulsifiers, isotonic saline, and pyrogen-free water.

The catalysts can be administered parenterally in combination with a pharmaceutically acceptable carrier such as corn oil, Cremophor EL or sterile, pyrogen-free water and a water-miscible solvent (e.g., ethyl alcohol) at a practical amount of the catalyst per dose. Preferably, the pharmaceutically-acceptable carrier, in compositions for parenteral administration, comprises at least about 90% by weight of the total composition. Parenteral administration can be by subcutaneous, intradermal, intramuscular, intrathecal, intraarticular or intravenous injection. The dosage by these modes of administration is usually in the range of from about 0.1 mg to about 20 mg per day.

Various oral dosage forms can be used, including such solid forms as tablets, capsules, granules and bulk powders. These oral forms comprise a safe and effective amount, usually at least about 5%, and preferably from about 25% to about 50% of the catalyst. Tablets can be compressed, tablet triturates, enteric-coated, sugar-coated, film-coated or multiple compressed, containing suitable binders, lubricants, diluents, disintegrating agents, coloring agents, flavoring agents, preservatives, flow-inducing agents, and melting agents. Liquid oral dosage forms include aqueous solutions, emulsions, suspensions, solutions and/or suspensions reconstituted from noneffervescent granules and effervescent preparations reconstituted from effervescent granules, containing suitable solvents, preservatives, emulsifying agents, suspending agents, diluents, sweeteners, melting agents, coloring agents, and flavoring agents. Preferred carriers for oral administration include gelatin, propylene glycol, ethyl oleate, cottonseed oil and sesame oil. Specific examples of pharmaceutically-acceptable carriers and excipients that may be used to formulate oral dosage forms containing the catalysts used in this invention are described in U.S. Pat. No. 3,903,297, Robert, issued Sep. 2, 1975, incorporated by reference herein. Techniques and compositions for making solid oral dosage forms are described in Marshall, "Solid Oral Dosage Forms," Modern Pharmaceutics, Vol. 7 (Banker and Rhodes, editors), 359-427 (1979), incorporated by reference herein.

It is to be understood that the above description is intended to be illustrative, and not restrictive. For example, the above-described embodiments (and/or aspects thereof) may be used in combination with each other. In addition, modifications may be made to adapt a particular situation or material to the teachings of the various embodiments of the invention without departing from their scope. Many other embodiments will be apparent to those of skill in the art upon reviewing the above description. The scope of the various embodiments of the invention should, therefore, be determined with reference to the appended claims, along with the full scope of equivalents to which such claims are entitled.

This written description uses examples to disclose the various embodiments of the invention, including the best mode, and also to enable any person skilled in the art to practice the various embodiments of the invention, including making and using any medicaments or pharmaceutical compositions and performing any incorporated methods. The patentable scope of the various embodiments of the invention is defined by the claims, and may include other examples that occur to those skilled in the art. Such other examples are intended to be within the scope of the claims if the examples have insubstantial differences from the literal languages of the claims.

EXAMPLES

Without further elaboration, it is believed that one skilled in the art can, using the preceding description, utilize the present invention to its fullest extent. The following specific examples are offered by way of illustration and not by way of limiting the remaining disclosure.

Example 1

Virtual Screening

The tools of structural bioinformatics were employed to identify potential sortilin antagonists. The primary technique employed in this research was high-resolution molecular docking, also known as virtual screening. The work was accomplished with the Autodock-4 program (Version 4.2, the Scripps Research Institute). Autodock 4 was used for large-scale experiments in which 1,200 potential ligands were screened at one time using high-performance computing. In a docking experiment, small molecules from an extensive database were tested within a grid on the receptor. As the molecules moved over the receptor protein, the interactions were scored by their energies, and the process was driven to progressively lower energy levels until a minimum was found. At the minimum, the test molecule has found a binding site, and is said to be "docked". Docking log files from Autodock 4 containing the information about each docked molecule was visualized in the computer to ascertain that the binding site made chemical sense. Docking experiments were conducted under high-throughput conditions, screening thousands of compounds in one experiment. Prior to the extensive virtual screening experiments, the model was validated by docking two peptides, neurotensin (NT) and the C-terminal ten amino acid sequence of progranulin (PRGNcterm) to the structure of sortilin (x-ray structure in the RCSB protein database 3F6K). Both of these peptides possess a leucine at their C-terminus, and this residue is known to be the binding determinant of neurotensin and PRGN with sortilin. In the case of NT, structures of 15 different conformations (NMR solution structures) were docked with sortilin. The C-terminal decapeptide of PRGN was studied with three different starting conformations, namely alpha helical, beta strand, and random coil. In both the NT and PRGNcterm docking experiments, Tripos'

Sybyl-X Surflex-Dock package was used (smaller scale) and yielded docked poses of exactly correct binding to sortilin. Hence, the docking model was validated and this showed that virtual screening could be predicted to result in reliable receptor-ligand interactions. Surflex-Dock experiments were conducted using a Silicon Graphics workstation.

The single-pose structures of sortilin bound to neurotensin and progranulin are depicted in FIGS. 2 and 3.

Example 2

ChemBridge CNS Database Screen

The ChemBridge Corporation maintains several extensive compound databases that are available to the public at no charge. For the work described in this application, the CNS (central nervous system) database was chosen. This database consists of over 54,000 compounds, and each of these is predicted to be orally bioavailable and to possess high penetrance of the blood-brain barrier. The database is furnished in SDF format. SDF files are directly readable into Surflex-Dock and Autodock-4.

Ten thousand compounds were screened by molecular docking from the ChemBridge CNS database. Of the 10,000 potential ligands, 100 were chosen based upon their low energy scores and high cluster populations, which indicated that multiple poses of a given ligand showed high-affinity docking. These 100 were visualized in their docked configurations on the sortilin receptor using the program VMD (Visual Molecular Dynamics, University of Illinois at Urbana-Champaign), and ligands demonstrating the best binding interactions (binding at the NT/PRGN site) were chosen. Ten such candidate compounds were identified and chosen for experimental testing in primary cortical neurons. These compounds were purchased commercially from the ChemBridge Company.

Example 3

Tissue

Murein E14-E15 cortices were dissected and removed to Hanks Balanced Salt Solution (HBSS) The tissue was dissociated with 0.05% trypsin in HBSS for 10 min at 37° C., and then filtered through a 70 pm cell strainer. Cells were plated on poly-D-lysine (PDL)-coated plates at $-3.2 \times 10^5$ cells/cm$^2$ in CEMEM (10% fetal bovine serum, 10% horse serum, 2 mM L-glutamine, and 1% penicillin/streptomycin) for 45 min in a 37° C. humidified tri-gas incubator (5% CO2 and 5% O2). The medium was changed to Neurobasal medium (Invitrogen, Carlsbad, Calif.) with a B27 supplement (Gibco) containing antioxidants (NB plus AO) to specifically enhance neuronal growth. After 3 days the media were half changed with NB plus AO. All treatments were done at day 5 with complete media change containing vehicle, SAHA (suberoyl anilide hydroxamic acid; Vorinostat), and test compounds at final concentrations ranging from 125 µM to 1 nM for 24 hours.

Example 4

Cell Viability Assay

The MTS non-radioactive cell viability assay employed [3-(4,5-dimethylthiazol-2-yl)-5-(3-carboxymethoxyphenyl)-2-(4-sulfophenyl)-2H-tetrazolium, inner salt with phenazine methosulfate added as an electron coupling reagent, MTS is bioreduced by cells into a formazan product that is soluble in tissue culture medium and can be measured at 490 nm. MTS was performed at 24 hours per manufacturer recommendations (Promega, G5421).

Example 5

Immunoblotting

Culture medium was collected and cells were lysed in lysis buffer containing 50 mM Tris-HCl, pH 7.5, 150 mM sodium chloride, 1% Nonidet P-40, 0.5% sodium deoxycholate, 1 mM sodium orthovanadate, 5 mM sodium fluoride, and a protease inhibitor cocktail. Sample concentrations were determined to ensure equal loading, placed in Laemmli sample buffer containing B-mercaptoethanol, and denatured at 100° C. for 5 min. Proteins were separated on a 4% stacking and 12% resolving SDS-PAGE Tris-glycine gel, transferred to polyvinylidene difluoride membrane (Millipore), and blocked in 5% instant milk or 5% bovine serum albumin in Tris-buffered saline with 0.1% Tween for 1 hour. For immunoblotting, primary antibodies were incubated overnight at 4° C. with 1/1000 tubulin (Developmental Studies Hybridoma), and 1/1000 Progranulin (ProteinTech Group). 15 µL of media was loaded from each sample. Ponceau red staining on the membrane before immunological probing was used to show equal loading to look for secreted progranulin and survival of motor neurons protein.

Results

Dot blots of the dosed culture extracts are shown in FIG. 5. It can be seen that compounds 1 and 5 (5 renumbered to 3) elicited accumulation of progranulin in the primary cortical neurons. Both of these compounds were found to be effective in extremely low doses, and were apparently non-toxic to the neurons. These results were confirmed by repeat triplicate experiments.

Effect on Survival Motor Neuron Protein (SMN)

Two of the compounds (2 and 4) were found to dramatically increase the cellular concentration of the survival motor neuron (SMN) protein in cortical neurons (FIG. 6). The SMN protein is known to be present at far below normal levels in patients with spinal muscular atrophy (SMA).

What is claimed is:

1. A method for treating a neurodegenerative disease selected from the group consisting of FTP, FTLD-U, and Alzheimer's disease with FTP, in a subject in need thereof, the method comprising administering a therapeutically effective amount of one or more pharmaceutical compositions comprising a pharmaceutically acceptable excipient and a pharmaceutically and physically acceptable amount of one or more compounds selected from the group consisting of:

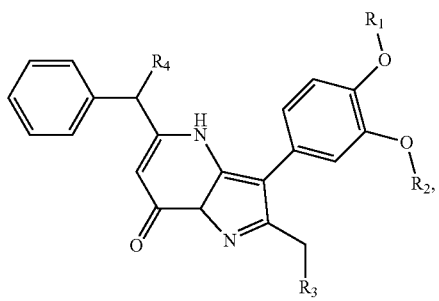

Chemical Formula I compound 1, $R_1$=$CH_3$, $R_2$=$CH_3$, $R_3$=H, and $R_4$=H;
or compound 5, $R_1$=$CH_3$, $R_2$=H, $R_3$=H, and $R_4$=H;
or a pharmaceutically acceptable salt thereof.

2. The method of claim 1 wherein the one or more compounds comprises Compound 1 or a pharmaceutically acceptable salt thereof.

3. The method of claim 1 wherein the one or more compounds comprises Compound 5 or a pharmaceutically acceptable salt thereof.

4. The method of claim 1 wherein the one or more pharmaceutical compositions is administered parenterally.

5. The method of claim 1 wherein the one or more pharmaceutical compositions is administered as part of an oleaginous suspension.

6. The method of claim 1 wherein the one or more pharmaceutical compositions is administered orally in the form of a tablet, capsule, granules, or bulk powder.

7. The method of claim 1 wherein the neurodegenerative disease is FTD.

8. The method of claim 1 wherein the neurodegenerative disease is FTLD-U.

9. The method of claim 1 wherein the neurodegenerative disease is Alzheimer's disease with FTD.

10. The method of claim 2 wherein the neurodegenerative disease is FTD.

11. The method of claim 2 wherein the neurodegenerative disease is FTLD-U.

12. The method of claim 2 wherein the neurodegenerative disease is Alzheimer's disease with FTD.

13. The method of claim 3 wherein the neurodegenerative disease is FTD.

14. The method of claim 3 wherein the neurodegenerative disease is FTLD-U.

15. The method of claim 3 wherein the neurodegenerative disease is Alzheimer's disease with FTD.

\* \* \* \* \*